United States Patent [19]

Arthur et al.

[11] Patent Number: 4,607,532

[45] Date of Patent: Aug. 26, 1986

[54] APPARATUS FOR DETERMINING THE BEHAVIOR OF POWDERED MATERIAL UNDER STRESS

[75] Inventors: Jonathan R. F. Arthur, Sevenoaks; Trebilcock Dunstan, Rickmansworth, both of England

[73] Assignee: University College London, London, England

[21] Appl. No.: 726,814

[22] Filed: Apr. 25, 1985

[30] Foreign Application Priority Data

Apr. 27, 1984 [GB] United Kingdom ............... 8410790

[51] Int. Cl.$^4$ ............................................. G01N 3/10
[52] U.S. Cl. ....................................... 73/819; 73/823; 73/825
[58] Field of Search ................. 73/819, 820, 823, 825

[56] References Cited

U.S. PATENT DOCUMENTS 3,423,995 1/1969 Scott et al. ..................... 73/819
3,728,895 4/1973 Shaw ............................. 73/819

FOREIGN PATENT DOCUMENTS 211849 8/1965 U.S.S.R. ........................ 73/819

*Primary Examiner*—Anthony V. Ciarlante
*Attorney, Agent, or Firm*—McAulay, Fields, Fisher, Goldstein & Nissen

[57] ABSTRACT

There is described an apparatus for determining the behaviour of powder of granular material under stress, comprising, at least one flexible boundary arranged to abut one face of a sample of the powder or granular material, means to apply stress to the sample through the flexible boundary, a detector to detect the position of the flexible boundary as the sample is stressed, and a control to adjust the position of the flexible boundary. The detector may comprise an electrical circuit, advantageously a make and break circuit. There is also described an apparatus for determining the behavior of powder or granular material under stress, comprising at least one flexible boundary arranged to abut one face of a sample of the powder or granular material, means to apply stress to the sample through the flexible boundary, and adjusting members attached to the flexible boundary to cause it to strain as the sample strains under the applied stress. Preferably, movement of the adjusting members of the flexible boundary automatically adjusts an adjacent flexible boundary.

6 Claims, 4 Drawing Figures

4,607,532

APPARATUS FOR DETERMINING THE BEHAVIOR OF POWDERED MATERIAL UNDER STRESS

BACKGROUND OF THE INVENTION

1. Field of the Invention

The present invention relates to an apparatus for determining the behaviour of powder or granular material under stress, in particular under low stress down to a minimum of zero, as for use in the design of free flowing storage hoppers.

2. Description of the Prior Art

A known device for testing the behaviour of powder or granular material is the so-called Jenike Cell. The Jenike Cell tests a cylindrical sample within rigid boundaries, assuming uniform stresses through the sample. The normal shear stresses on a horizontal plane within the sample are calculated from two external force measurements. Then, by assuming the inclination of the principal stresses to this horizontal plane, design data are obtained. It is widely recognised that neither of these assumptions can be successfully made in the Jenike Cell without elaborate precautions. The application of uniform stresses to rigid boundaries can never be assumed and at verylow stress levels the error introduced by mechanical linkages will be unacceptable.

In the field of soil mechanics, there is a class of shear testing apparatus which impose boundary stresses through flexible boundaries, see for example Arthur, Chua & Dunstan, Geotechnique Vol. 27. No. 1,1977 pages 74 to 87.

These flexible boundary apparatus approach the ideal of applying uniform and directly measured stresses when the distortions of the samples are small. However, when a very low stresses are required, the stress required to distort even the lightest flexible membrane will represent a serious error which cannot be easily quantified.

BRIEF SUMMARY OF THE INVENTION

Preferably, a bag is supported around an adjustable frame which is contacted by a backing plate and is connected to adjusting members.

According to a second aspect of the invention, there is provided an apparatus for determing the behaviour of powder or granular material under stress, comprising:

at least one flexible boundary arranged to abut one face of a sample of the powder or granular material;

means to apply stress to the sample through the flexible boundary; and adjusting members attached to the flexible boundary to cause it to strain as the sample strains under the applied stress.

Preferably, movement of the adjusting members of the flexible boundary automatically adjusts an adjacent flexible boundary.

Preferably, in both aspects of the invention, the flexible boundary is the front face of a pressurized bag and the control adjusts the position of a backing plate arranged on the back of the bag.

Advantageously, the sample has a number of planar surfaces and a flexible boundary is provided for some or all of the planar surfaces.

Preferably, the bag is supported around an adjustable frame which is contacted by the backing plate. The frame may be connected to the adjusting members.

Most preferably, on the face or faces of the sample which are not stressed by the said stress applying means, there is provided a flexible sheet which strains along with that face or faces. The flexible sheet is preferably connected to the adjusting member and backing plates of the other faces.

The invention has the advantage that since the flexible boundary can strain at the same rate as the surface of the sample strains, then the surface tractions which would otherwise develop during deformation of the sample can be eliminated. Also, the flexible boundary can be maintained planar and therefore the stress must be uniformly applied to the sample. Further, as the flexible boundary is maintained planar, it remains a fixed distance from the backing plate and therefore displacement of the backing plate, which can easily be measured, corresponds to displacement of the sample face.

The invention can easily cope with relatively large strains at very low stress levels and can greatly reduce the testing time required to obtain design data compared to the time using a Jenike Cell.

DETAILED DESCRIPTION

Figure 1:
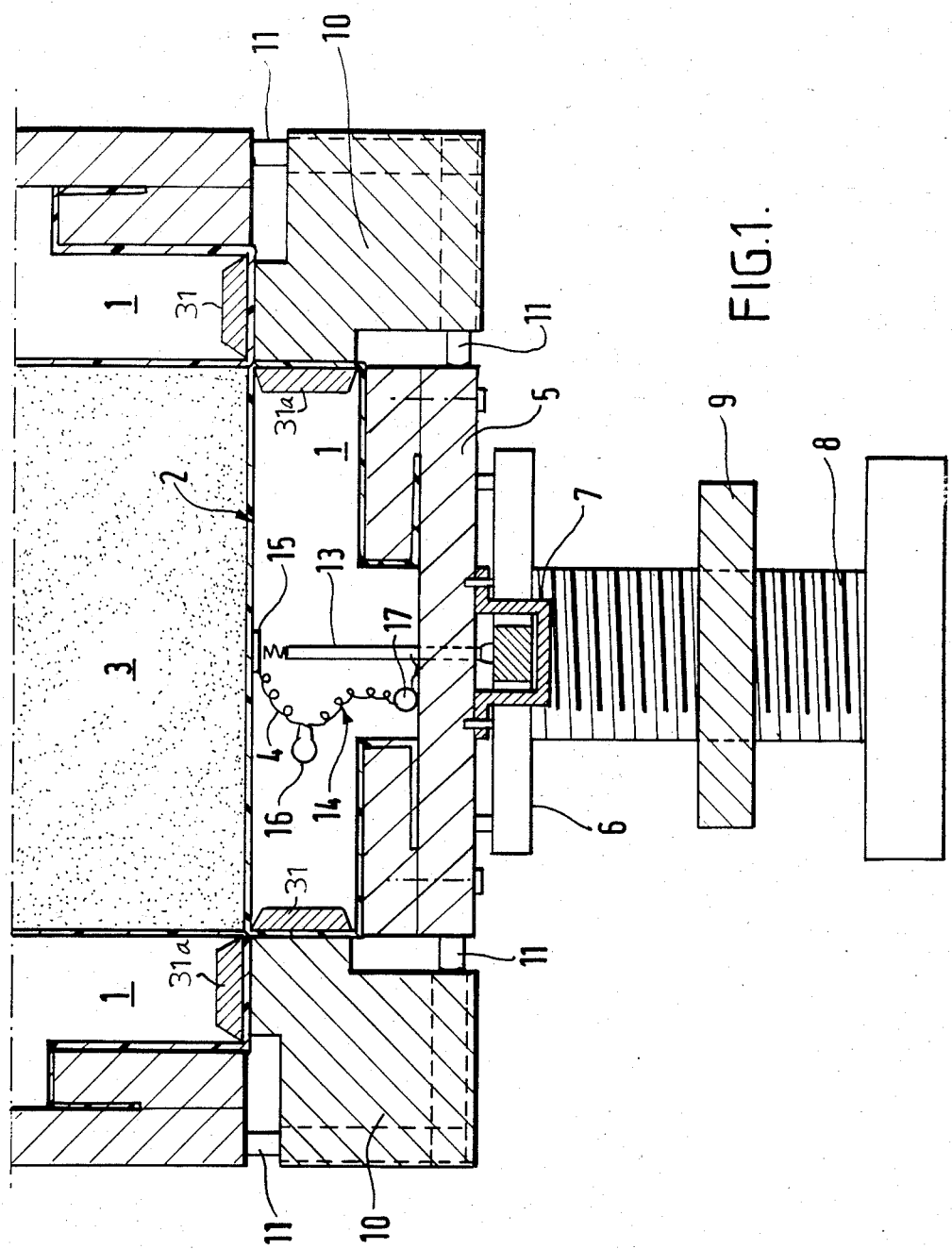
FIG. 1 is a schematic horizontal sectional view through part of an apparatus of the invention.

The apparatus of FIG. 1 comprises a pressurized bag 1, the front face 2 of which provides the flexible boundary contacting one face of the sample 3 of powder or granular material. The pressure in the bag 1 applies a stress to the sample 3 through the front face 2.

Figure 2:
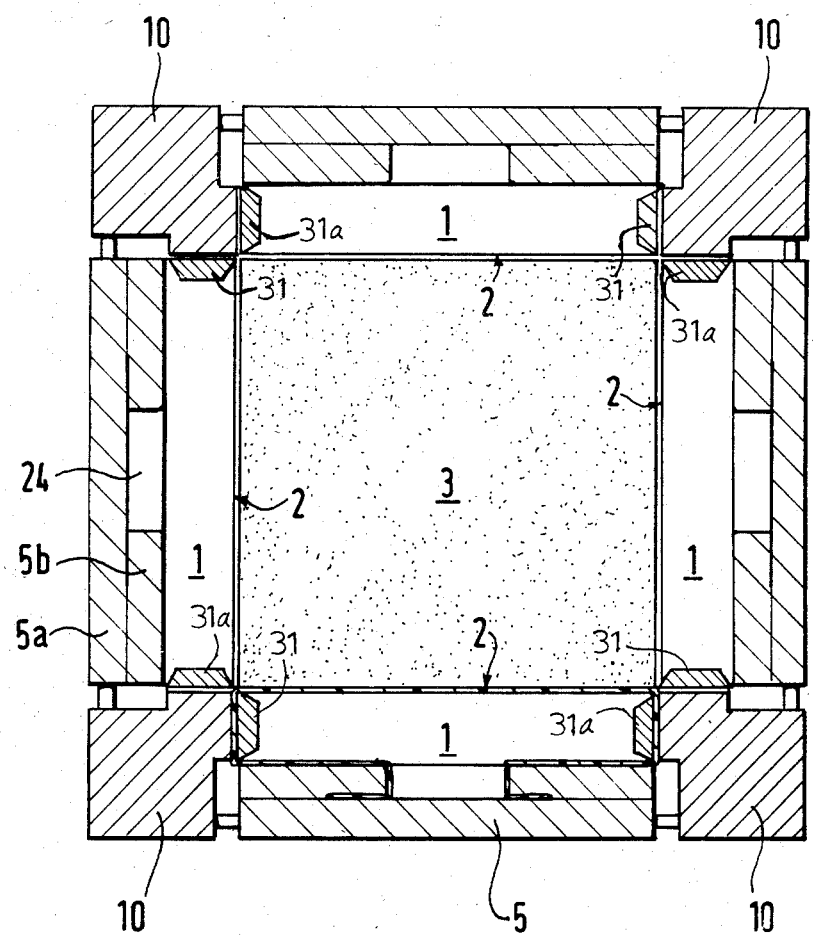
FIG. 2 is another horizontal section through the apparatus.

As more clearly shown in FIG. 2, the apparatus has four pressurized bags 1 on the four lateral faces of a cubical sample 3.

The apparatus also comprises circuit 4 which acts as a detector to detect and indicate the position of the front face 2 as the sample is stressed.

At the back of each bag 1 there is arranged a backing plate 5 which is pressed by a thrust plate 6 to which it is held by a retaining fastening 7. The thrust plate 6 is driven by a screw-drive 8 which is mounted in a fixed reaction plate 9.

The movable backing plate 5 provides the control to adjust the position of the flexible boundary 2 in response to the output of the detector 4.

Figure 3:
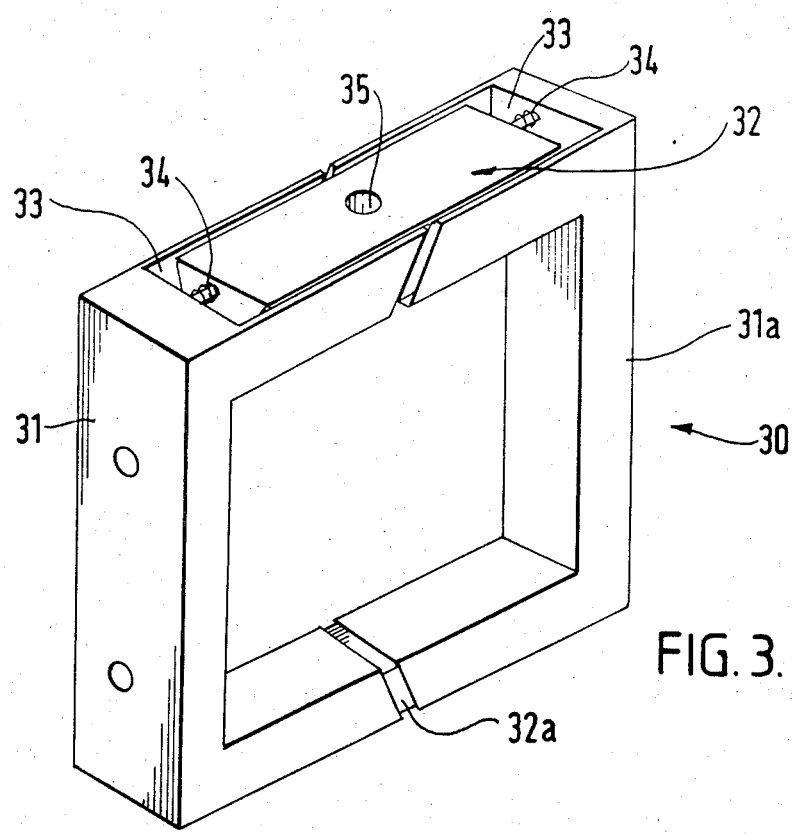
FIG. 3 is a perspective view of the frame.

The bag 1 is supported on a rectangular frame 30 which is shown in move detail in FIG. 3. The frame 30 comprises two C-shaped members 31, 31a, the top and bottom arms of which are recessed. Bridges 32, 32a fit into the recesses 33 at the top and bottom of the frame, these bridges being mounted on springs 34 which extend along the length of the recesses. The members 31, 31a can thus move apart, but the rectangular shape of the frame is preserved by the bridges interconnecting the members. The top bridge 32 has a hole 35 approximately half way along its length.

The bag 1 is fitted over the frame 30 and is then clamped between the two plates 5a, 5b which form the backing plate 5. One of the plates has a central aperture 24 through which the neck of the bag 1 passes before being clamped.

Along the length of each of its sides, the bag 1 on frame 30 is supported by a guide 10. The sides of the frame are fixed to the guides, for example by screws. The guides 10 are adjustably connected to the backing plate 5 via rods 11 fixed to the backing plate which slide in slots in the guide.

As is most clearly seen in FIG. 2, each guide 10 supports the sides of two bags and is adjustably connected to two backing plates. Thus, when the backing plate 5 of one bag is moved forward, say, not only will the front face of that bag move forward, but also the sides of the frames of the adjacent bags will move in the same direction since the guides which move forward with the backing plate are connected to the frames of the adjacent bags and slide on the rods 11 of the backing plates of those adjacent bags.

It will be appreciated that the design of the frame 30 enables the bag to stretch laterally when the guides 10 are adjusted but prevents the rubber bag straining vertically and thus compensates for any Poisson Ratio effect of the rubber.

Circuit 4 comprises a contact make and break sustem including a screw set rod 13 adjustably mounted in the backing plate 5 and lead 14 connected to a contact disc 15 glued to the back face of the bag face 2. Connected in the lead 14 is a bulb 16 and a battery 17. The circuit is made when the spring at the forward end of the rod 13 contacts the disc 15. The current is broken when the disc 15 moves away from the end of the rod 13. Thus, slight movement of the flexible boundary 2 can make and break circuit 4.

Each pressure bag 1 is connected to a precision air valve and a precise measuring device (not shown), for example a manometer or pressure transducer system.

Each bag 1 is generally composed of rubber, such as natural latex. Front face 2 is unreinforced and is relatively thin.

The sample 3, the retaining guides 10, the pressure bags 1 and the backing plate 5 all rest on a base plate (not shown) to which the four reaction plates 9 are fixed. Beneath the sample, a water filled pressure bag is provided in a recess in the base plate. Through this pressure bag, which provides a horizontal flexible boundary, the intermediate stress may be set or monitored. Complete filling of this water bag ensures that the direct strain in the vertical direction is negligible.

Above the sample is fixed an upper transparent acrylic plate fixed on top of the reaction plates 9. This horizontal transparent plate reacts the loading provided by the intermediate principal stress and allows the bulbs 16 within the pressure bags to be seen, when illuminated, through the holes 35 in the frames 30.

Figure 4:
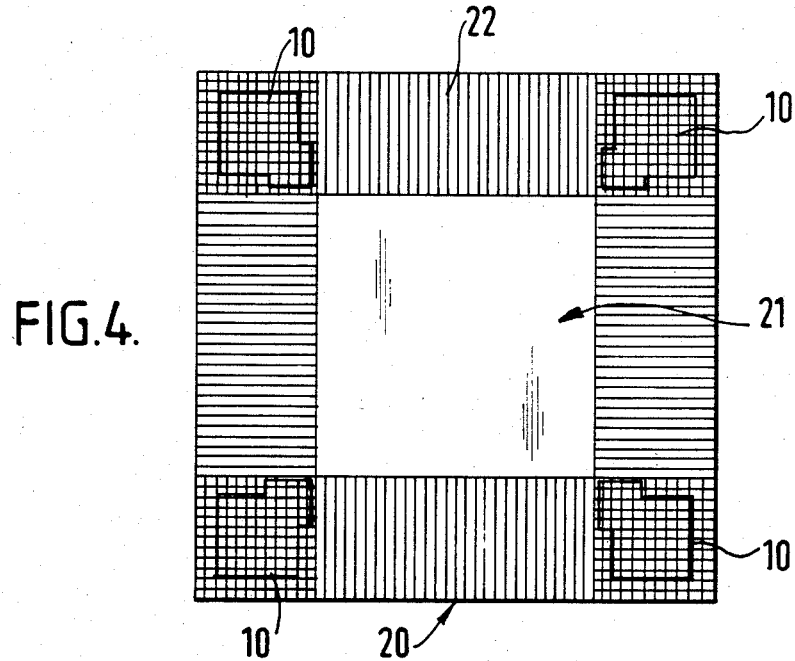
FIG. 4 is a plan view showing the flexible sheet.

Between the top and bottom of the sample and the upper and lower plates respectively are introduced rubber sheets 20, as illustrated in plan view in FIG. 4. The central part 21 of the sheet in contact with the upper or lower sample face is of thin unreinforced rubber, while the sections 22 at the sides are reinforced. by non-stretch fibres 23 in a direction at right angles to the edges of the face of the sample which the sheet covers. At the corners, the section 22 overlap so that the corner areas are reinforced in two directions. The sheet is secured to the four lateral backing plates so that it is stretched in both directions in the plane of the sheet. Thus, movement of the backing plates adjusts the upper and lower sheets 21 to ensure that no shear stresses develop on the upper and lower faces of the sample. The method of reinforcing rubber sheets is known, for example from the article "On the Making of Rubber Sheets" by Menzies and Phillips, Geotechnique March 1972.

To use the testing apparatus of the invention, firstly an amount of powder or granular material is compressed in layers in a former by the application of an accurately controlled pressure to produce a cubical sample. The former is removed after the pressure bags and their backing plates and lateral guides are positioned around the sample as previously described. Small initial pressures, which are sufficient to ensure stability of the sample but are not large enough to cause the sample to deform, are applied through all the flexible boundaries. Generally, the water in the bottom pressure bag will be isolated to maintain constant volume to prevent vertical direct strain in the sample.

Pressure is then applied to the lateral bags 1. Two opposite bags apply the major principal stress while the other two opposite bags apply the minor principal stress. The pressure in each bag should be transmitted to the sample face through the undistorted, front face 2 of each bag. The front face 2 should remain planar so that the stresses applied are uniform. The front face 2 and rubber sheet 20 should strain with the strain of the sample face so that shear stressses are not imposed on any of the faces of the sample. It will be appreciated that the application of uniform principal stresses without shear stresses provides much greater accuracy to the testing procedure.

After the initial pressures are applied, the screw set rod 13 in each bag is adjusted such that the bulb just goes out when the bag is applying the minor principal stress, and the bulb just goes on when the bag is applying the major principal stress.

As a small increment of pressure is applied to the bags supplying the major principal stress, the front face 2 of each bag tends to balloon out and the bulb goes out. To counteract this slight deviation of the front face from being planar, the backing plate 5 is advanced until the light comes on again.

With the bags supplying the minor principal stress, the bags tend to balloon inwards. To regain the planar position of the front face 2 in this case, the backing plate is withdrawn until the light goes out again. The light going on or off in each case is an immediate indication that the front face 2 has deviated from being planar.

Thus, the control of internal pressure and of the position of the backing plate affords a system which maintains the front face of the sample substantially flat while also controlling the stress applied to the sample. As the front face of the pressure bag is planar, the pressure in the bag must be fully transmitted to the sample, whatever the tension in the front face.

The increasing or decreasing areas of the deforming sample faces are matched by the movement of the lateral guides 10 to stretch or contract the flexible boundaries. The faces of the sample to which the principal major stresses are applied will tend to increase in area while the other two faces to which the minor principal stresses are applied tend to decrease in area.

As the backing plates of the bags supplying the major principal stress are moved forward during testing, the guides to which the front faces of the bags applying the minor principal stress are attached move together. Thus those front faces shrink to follow the sample faces. Similar, as the backing plates of the bags applying the minor principal stresses are moved backwards, the guides to which the front faces of the bags applying the major principal stresses are attached move apart. Thus, the front faces of the bags applying the major principal stress stretch with the sample faces.

Thus the increasing or decreasing areas of the sample faces are matched by the changing dimensions of each flexible boundary so that surface tractions, which would otherwise result in serious errors, do not arise.

Markers embedded in the top face of the sample cube can be photographed, thus quantitively recording the sample strain distribution which is imposed.

It should also be noted that since the front face 2 of each bag 1 is maintained planar it also maintains a known fixed distance from the backing plate. Therefore movement of the backing plate, which can easily be measured directly, gives the displacement of the corresponding front face of the bag. Thus strains on the sample can easily and directly be measured using dial gauges on the backing plates.

The detector which is provided by the circuit 4 also can be used to indicate yield very direct manner, since the contact pad 15 directly follows the movement of the face of the sample. In the case of the bags applying the major principal stress, failure of the light to come on as the backing plate is driven forward indicates continuous yield. In the other case, where the bags apply the minor principal stress, continuous yield is indicated by failure of the light to go out whilst the backing plate is being withdrawn.

The dial gauge readings of movement of the backing plates of each bag can be converted into major and minor principal strains whilst a test is actually in progress.

The four pressurized bags are filled with air where the stresses to be applied are very low. Where higher stresses are applied, water may be introduced into the bags instead as the stresses caused by the weight of the water are neglegible.

Naturally, the described testing apparatus may also be used to test the properties of soil.

What we claim is:

1. An apparatus for determining the behaviour of powder or granular material under stress, comprising:
    four flexible boundaries arranged to abut four faces of a cuboid sample of the powder or granular material;
    means to apply stress to the sample through the flexible boundaries in two perpendicular directions;
    adjusting members arranged at the lateral edges of the said faces and each operatively connected with two adjacent flexible boundaries; and
    control means to adjust the said adjusting members whereby adjustment of each said member adjusts the two said adjacent flexible boundaries to allow them to strain as the sample strains under the applied stress.

2. An apparatus according to claim 1, wherein each flexible boundary is in the front face of a pressurized bag which is supported by a backing plate arranged on the back of the bag, the backing plate being adjustably connected to the two adjusting members at the edges of each flexible boundary.

3. An apparatus according to claim 2, wherein the or each bag is supported around an adjustable frame which is contacted by the backing plate, and connected to the adjusting members.

4. An apparatus according to claim 2, wherein on the two faces of the sample which are not stressed by the said stress applying means, there is provided a flexible sheet which is adapted to strain along with those two faces, the flexible sheet being connected to the adjusting members and the backing plates of the stressed faces.

5. An apparatus according to claim 1, further comprising a detector to detect the position of each flexible boundary as the sample is stressed.

6. An apparatus according to claim 5, wherein the detector comprises an electrical make and break circuit.

* * * * *